US012710393B2

(12) United States Patent
Babic et al.

(10) Patent No.: US 12,710,393 B2
(45) Date of Patent: Aug. 18, 2026

(54) METHOD FOR PREPARING A WORKING ELECTRODE

(71) Applicant: Roche Diabetes Care, Inc., Indianapolis, IN (US)

(72) Inventors: Branislav Babic, Ludwigshafen (DE); Alexander Steck, Hirschberg (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 245 days.

(21) Appl. No.: 18/310,770

(22) Filed: May 2, 2023

(65) Prior Publication Data

US 2023/0273145 A1 Aug. 31, 2023

Related U.S. Application Data

(63) Continuation of application No. PCT/EP2021/082273, filed on Nov. 19, 2021.

(30) Foreign Application Priority Data

Nov. 23, 2020 (EP) .................................... 20209219

(51) Int. Cl.

| | |
|---|---|
| ***G01N 27/327*** | (2006.01) |
| ***A61B 5/145*** | (2006.01) |
| ***A61B 5/1486*** | (2006.01) |
| ***C12Q 1/00*** | (2006.01) |
| ***C12Q 1/26*** | (2006.01) |

(52) U.S. Cl.

CPC ......... *G01N 27/3276* (2013.01); *C12Q 1/006* (2013.01); *C12Q 1/26* (2013.01); *A61B 5/14546* (2013.01); *A61B 5/1486* (2013.01); *A61B 2562/125* (2013.01)

(58) Field of Classification Search

CPC ............ G01N 27/3272; G01N 27/3276; A61B 2563/125; B05D 1/26

See application file for complete search history.

(56) References Cited

U.S. PATENT DOCUMENTS

| | | | | |
|---|---|---|---|---|
| 9,829,459 | B2 * | 11/2017 | Zhu | C12Q 1/006 |
| 2002/0020632 | A1 * | 2/2002 | Douglas | G01N 27/3272 205/777.5 |
| 2008/0027287 | A1 | 1/2008 | Rajiv et al. | |

(Continued)

FOREIGN PATENT DOCUMENTS

| | | |
|---|---|---|
| CN | 110651183 | 1/2020 |
| CN | 111870238 | 11/2020 |

(Continued)

OTHER PUBLICATIONS

Cannula Definition & Meaning—Merriam-Webster (Year: 2026).*
International Search Report and Written Opinion of related PCT/EP2021/082273 mailed Mar. 9, 2022.

*Primary Examiner* — C. Sun
(74) *Attorney, Agent, or Firm* — Woodard, Emhardt, Henry, Reeves & Wagner, LLP

(57) ABSTRACT

The present invention relates to a method for the preparation of a working electrode, the method comprising application of a sensing material in several steps. Further, the present invention relates to an analyte sensor comprising the working electrode as well as to the use of the analyte sensor for detecting at least one analyte in a sample.

22 Claims, 3 Drawing Sheets

(56) References Cited

U.S. PATENT DOCUMENTS

| | | | | |
|---|---|---|---|---|
| 2010/0075347 | A1* | 3/2010 | Dasaratha | G01N 29/022 435/7.33 |
| 2017/0188922 | A1* | 7/2017 | Lee | C08G 18/3857 |
| 2018/0017883 | A1* | 1/2018 | Azzam | G03G 9/133 |
| 2020/0178801 | A1* | 6/2020 | Nazari | A61B 5/7275 |
| 2020/0220168 | A1* | 7/2020 | Ashford, II | C23C 28/023 |

FOREIGN PATENT DOCUMENTS

| | | |
|---|---|---|
| KR | 10-2020-0118805 | 10/2020 |
| WO | WO 2009120240 | 10/2009 |
| WO | WO 2019035073 | 2/2019 |

* cited by examiner

METHOD FOR PREPARING A WORKING ELECTRODE

TECHNICAL FIELD

The present invention generally relates to a method for the preparation of a working electrode and to an analyte sensor comprising the working electrode as well as to the use of the analyte sensor for detecting at least one analyte in a sample. In particular, the invention relates to a method for the preparation of a working electrode, the method comprising application of a sensing material.

BACKGROUND ART

Monitoring certain body functions, more particularly monitoring one or more concentrations of certain analytes, plays an important role in the prevention and treatment of various diseases.

Along with so-called point measurements in which a sample of a body fluid is specifically taken from a user and investigated for the analyte concentration, continuous measurements are increasingly becoming available. Hence, there is an increasing demand for accurate analyte sensors that enable reliable and cost-efficient analyte detection from a body fluid or other samples. An analyte sensor for determining the concentration of an analyte under in vivo conditions is known from WO 2010/028708 A1. Another example of such sensor is disclosed in WO 2012/130841 A1. Moreover, WO 2007/147475 A1 discloses an amperometric sensor configured for implantation into a living body to measure the concentration of an analyte in a body fluid. An alternative sensor element is disclosed in WO 2014/001382 A1.

U.S. Pat. No. 10,327,677 B2 discloses analyte sensing devices comprising two or more sensing elements. The application of a continuous layer of sensing material is not disclosed.

U.S. Pat. No. 9,309,550 B2 discloses analyte sensors having electrodes comprising conductive nanotubes and methods of using them. The sensing material is applied as very thin layer and a thick analyte modulating layer disposed on the analyte sensing layer, wherein the analyte modulating layer modulates the diffusion of glucose therethrough.

U.S. Pat. No. 9,829,459 B2 discloses a method for depositing reagent on an electrochemical test sensor. The method includes application of droplets.

Applying sensing material on a conductive layer on a working electrode of an analyte sensor is not trivial. The sensing material is hydrophilic, whereas the conductive layer, e.g. carbon, is hydrophobic. Thus, wetting of the substrate surface by the sensing material does practically not take place. As a result, the applied layer of sensing material may disperse, i.e. having an increased thickness in the center of the application area and a decreased thickness at the edges. This may result in an insufficient layer thickness of the sensing material and a negative sensor drift.

The problem to be solved by the present invention is to provide a method for the preparation of a working electrode that avoids the above-mentioned disadvantages. In particular, the present invention aims in providing a preparation method resulting in a sensing material structure having an increased thickness at its edges on the working electrode.

It is therefore desirable to provide methods for preparing a working electrode and an analyte sensor, which address the above-mentioned technical challenges. It is further desirable to provide a working electrode and an analyte sensor which have a stable sensitivity but can be manufactured at low cost, e.g. by using a preparation process that produces a sensing material layer having an increased thickness at its edges.

SUMMARY

This problem is addressed by a method for the preparation of a working electrode and an analyte sensor comprising the working electrode, with the features of the independent claims. Advantageous embodiments, which might be realized in an isolated fashion or in any arbitrary combination are listed in the dependent claims and throughout the specification.

The method according to the invention is advantageous as it allows the manufacturing of a working electrode, which may be comprised in an analyte sensor with an increased thickness at its edges and an almost constant sensor sensitivity, which shows little or no changes during the lifetime of the sensor. Further, the sensor manufacturing is faster than known manufacturing methods and a subsequent laser ablation step is not necessary. Furthermore, the steep edges of the applied layer of sensing material are advantageous since the enzyme present in the sensing material is not depleted during use.

According to the present invention, a method for the preparation of a working electrode on a sensor substrate is disclosed. The working electrode may be part of an analyte sensor.

The method comprises the following steps, which specifically may be performed in the given order. Further, if not indicated otherwise, two or more process steps may be performed simultaneously or partially simultaneously. Further, one or more than one or even all of the method steps may be performed once or more than once or even repeatedly or continuously. The method may further comprise additional method steps, which are not listed specifically.

According to a first aspect of the invention, a method for manufacturing a working electrode of an analyte sensor is provided, wherein the method comprises the following steps:

(a) providing a substrate comprising
  a first side and a second side,
  at least one conductive material positioned on the first side of the substrate, (b) applying a sensing material to an application area on the first side of the substrate, and (c) obtaining the working electrode of the analyte sensor on the first side of the substrate, wherein the sensing material may comprise at least one enzyme and at least one crosslinker, wherein the sensing material is applied in step (b) in a wet layer thickness of greater than about 20 μm in a single application.

In certain embodiments, step (b) is performed only once.

In an embodiment, the sensing material is applied in step (b) in a wet layer thickness of greater than about 70 μm in a single application.

In certain embodiments, the method further comprises:

drying the applied sensing material.

In certain embodiments, step (c) of the method further comprises:

curing the applied sensing material wherein at least a part of the sensing material is crosslinked.

In certain embodiments, step (c) of the method further comprises:

coating the sensing material with at least one further polymer layer.

A further aspect of the invention relates to a method for manufacturing an analyte sensor comprising manufacturing the working electrode as described above and providing at least one further electrode.

Still a further aspect of the invention relates to an analyte sensor comprising:

(i) a substrate comprising
  - a first side and a second side, and
  - at least one conductive material positioned on the first side of the substrate, (ii) a working electrode comprising a sensing material, which at least partially covers the first side of the substrate, wherein the sensing material forms a layer on the first side of the substrate, wherein the layer of sensing material comprises at least on edge generated by the application of the sensing material onto an application area on the substrate, wherein the sensing material may comprise at least one enzyme and at least one crosslinker, wherein the layer of sensing material has a dry average total thickness in the range from about 3 μm to about 8 μm, particularly from about 3 μm to about 6 μm and more particularly from about 4 μm to about 5 μm, and wherein the dry total thickness of the layer of sensing material along at least one of said edges is substantially the same or is increased compared to the dry average total thickness of the layer of the sensing material.

In certain preferred embodiments, the sensing material comprises at least one enzyme and at least one crosslinker.

In certain alternative embodiments, the sensing material comprises at least one enzyme and does not comprise a crosslinker.

Still a further aspect of the present invention relates to an analyte sensor comprising a working electrode as described above and at least one further electrode.

Definitions

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation, in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

DETAILED DESCRIPTION

The present invention relates to a method for manufacturing of a working electrode of an analyte sensor as described above and to a working electrode as described above.

The term "working electrode" as used herein, is a broad term and is to be given its ordinary and customary meaning to a person of ordinary skill in the art and is not to be limited to a special or customized meaning. The term specifically may refer, without limitation, to the electrode of the analyte sensor that is sensitive for the analyte. The working electrode may be disposed on the at least one first side of the at least one sensor substrate. In particular, the working electrode comprises at least one conductive material and at least one sensing material, wherein said at least one sensing material is applied to an application area on the conductive material on the first side of the sensor substrate. In certain embodiments, a single layer of sensing material is applied during step (b). Particularly, the layer of sensing material is applied by cannula-coating.

The sensing material is applied during step (b) in a wet layer thickness of greater than about 20 μm, e.g. about 20 μm to about 200 μm, in particular, in a wet layer thickness of greater than about 70 μm, e.g. about 70 μm to about 200 μm in a single application. For example, the wet layer thickness may be about 75 μm or more, particularly about 75 μm to about 200 120 μm, about 80 μm to about 110 μm or about 90 μm to about 100 μm. The wet layer thickness of a sensing material layer may be determined by the ratio of the flow rate of the sensing material from the cannula to the speed of the substrate relative to the cannula and the width of the layer according to the following formula:

$$T=FR/S/W,$$

wherein

T is the wet layer thickness in mm.

FR is the flow rate in ml/s

S is the speed of the substrate relative to the cannula in mm/s and

W is the width of the layer of the sensing material in mm.

The width of the layer of the sensing material may be determined by light scanning microscopy, in particular by laser scanning microscopy. Suitable light scanning microscopes are known and are, for example a Keyence microscope VK-9710 or a FRT MicroProf.

The wet layer thickness relates to the thickness of the sensing material before it is dried. For application of the sensing material in step (b) the sensing material preferably comprises at least one solvent. A suitable solvent is, for example, selected from the group consisting of protic solvents, in particular water. The wet layer thickness relates to the thickness of the sensing material which comprises the at least one solvent, in particular water.

After application, the wet layer of sensing material is dried. Thus, the at least one solvent, in particular water, evaporates. In certain embodiments, after drying, the total sensing material applied onto the substrate has a dry average total thickness in the range from about 3 μm to about 8 μm, particularly from about 3 μm to about 6 μm and more particularly from about 4 μm to about 5 μm.

In the method of the invention, a sensing material is preferably applied in a single step to an application area positioned on the first side of a substrate. In a preferred embodiment, step (b) is carried out only once. Thus, in particular, step (b) may not be repeated. After drying, the sensing material forms a layer on the first side of the substrate, wherein the layer of sensing material comprises at least one edge generated by the application of the sensing material onto the substrate, particularly onto an application area on the substrate. The term "application area" as used herein, is a broad term and is to be given its ordinary and customary meaning to a person of ordinary skill in the art and is not to be limited to a special or customized meaning. The term specifically may refer, without limitation, to the whole area of the first side of the substrate where the sensing material has been applied. In certain embodiments, the application area is in the range of about 0.1 $mm^2$ to about 2 $mm^2$, particularly about 0.6 $mm^2$. In certain embodiments, the layer of the sensing layer is applied in width of about 200 μm to about 1500 μm, of about 250 μm to about 600 μm, particularly from about 300 μm to about 500 μm, more particularly about 400 μm.

After drying, a layer of sensing material is formed on the first side of the substrate, wherein the layer of sensing material comprises edges generated by the application of the sensing material on the application area. In this context, it should be noted that the term "edges" exclusively relates to the edges generated by the application of the sensing material on the application area and not to edges generated by cutting the working electrode or the analyte sensor into smaller pieces.

Typically, the layer of sensing material in a working electrode or an analyte sensor comprises more than one edge, e.g. 2 edges, particularly 2 opposing edges, 3 edges or 4 edges generated by the application of the sensing material on the application area. According to the present invention, the dry total thickness of the layer of sensing material along at least one of the edges of the application area, particularly along all edges of the application area, is substantially the same or is increased compared to the dry average total thickness of the layer of the sensing material.

In certain embodiments, the dry total thickness of the sensing material at the edges of the application area is substantially the same compared to the dry average total thickness of the layer of the sensing material. For example, the dry total thickness of the sensing material at least along one of the edges of the application area, particularly along all edges of the application area, may be at least about 75%, at least about 80%, at least about 85%, at least about 90%, at least about 95% and up to about 150%, or up to about 125% compared to the dry average total thickness of the layer of the sensing material (being defined as 100%). In certain embodiments, the dry total thickness of the sensing material at the edges of the application area differs not more than about 1 μm, more particularly not more than about 0.5 μm compared to the dry average total thickness of the layer of the sensing material.

In certain embodiments, the dry total thickness of the sensing material at the edges of the application area is substantially increased compared to the dry average total thickness of the layer of the sensing material. For example, the dry total thickness of the sensing material at least along one of the edges of the application area, particularly along all edges of the application area, may be at least about 125% or at least about 150% compared to the dry average total thickness of the layer of the sensing material (being defined as 100%). In these embodiments, the dry total thickness of the sensing material at least along one of the edges of the application area, particularly along all edges of the application area, may be up to about 250% or up to about 200% compared to the dry average total thickness of the layer of the sensing material (being defined as 100%). In certain embodiments, the dry total thickness of the sensing material at the edges of the application area shows an increase of more than about 0.5 μm, more particularly of more than about 1 μm compared to the dry average total thickness of the sensing material.

The dry average total thickness of the sensing material may be determined by light scanning microscopy, in particular by laser scanning microscopy. Suitable light scanning microscopes are known and are, for example a Keyence microscope VK-9710 or a FRT MicroProf. The dry thickness is determined along the scanning range and then the average of the dry total thicknesses is calculated by methods known to the skilled person to obtain the dry average total thickness.

To determine the thickness of the sensing material along an edge, the dry thickness is determined as described above. The edges are then determined in the range of the outermost boundary of the layer inwards. The outermost boundary of the layer is, for example, the outermost third of the layer.

In particular embodiments, the edges of the sensing layer are steep. For example, the angle between the surface of the substrate and the edge of the sensing material layer may be at least about 60°, at least about 75° or even at least about 80°.

In certain embodiments, a cross-section of the layer of the sensing material is substantially a rectangle optionally having an increased height at edges generated by the application of the sensing material onto the application area. In certain embodiments, the shape of the layer of the sensing material is substantially a cuboid optionally having an increased height at edges generated by the application of the sensing material onto the application area.

In certain embodiments, the sensing material is applied to the application area on the first side of the substrate and remains on the complete application area during the further steps for manufacturing. In particular embodiments, the sensing material is preserved on the complete application area and not subjected to a treatment where a portion of the sensing material is removed, e.g. by laser ablation. In presently less preferred embodiments, the sensing material is removed from a first portion of the application area and is preserved on a second portion of the application area.

In certain embodiments, the sensing material is applied continuously to the substrate. In these embodiments, the substrate may be a raw substrate material, particularly a sheet or a roll, e.g. having a length of about 10 cm or more such as about 30 cm, onto which the layer of sensing material is continuously applied. After application, particularly after drying, the raw substrate material may be cut into pieces having the desired size.

The working electrode may be comprised in an analyte sensor. The analyte sensor typically comprises additionally a further electrode, such as for example a counter electrode and/or a reference electrode. The layer of sensing material may be present on the working electrode only and may typically be absent from any further electrodes, e.g. the counter electrode and/or the reference electrode may not comprise a layer of the sensing material.

In addition, the present invention discloses a method for manufacturing an analyte sensor. The method for manufacturing of an analyte sensor comprises the method for manufacturing a working electrode on a substrate as disclosed herein and a step of providing at least one further electrode.

The analyte sensor may be configured for at least partial implantation, specifically transcutaneous insertion, into a body tissue of a user; more specifically the analyte sensor may be configured for continuous monitoring of the analyte, even more specifically the analyte sensor may be configured for continuous glucose monitoring.

The terms “user” and “subject” are used interchangeably herein. The terms may in particular relate to a human being.

The term “analyte sensor” as used herein is a broad term and is to be given its ordinary and customary meaning to a person of ordinary skill in the art and is not to be limited to a special or customized meaning. The term specifically may refer, without limitation, to an arbitrary element or device configured for detecting or for measuring the concentration of the at least one analyte. The analyte sensor specifically may be an analyte sensor suitable for at least partial implantation into a body tissue of a user, more specifically an analyte sensor for continuous monitoring of the analyte.

In particular embodiments, the analyte sensor of the invention is an electrochemical sensor comprising the working electrode obtainable according to the method of the present invention and at least one further electrode and respective circuitry. More particularly, the sensor is an amperometric electrochemical sensor comprising the at least one working electrode. Typically, the analyte sensor comprises at least one further electrode, particularly a counter electrode and/or a reference electrode or a combined counter/reference electrode. Even more particularly, the sensor comprises precisely one further electrode. Even more particularly, the sensor is a two-electrode sensor comprising precisely one working electrode and precisely one combined counter/reference electrode.

The working electrode is sensitive for the analyte to be measured at a polarization voltage which may be applied between working and reference electrodes and which may be regulated by a potentiostat. A measurement signal may be provided as an electric current between the counter electrode and the working electrode. A separate counter electrode may be absent and a pseudo reference electrode may be present, which may also work as a counter electrode. Thus, an analyte sensor typically may comprise a set of at least two, in an embodiment a set of three electrodes. Particularly, the sensing material is present in the working electrode only.

Particularly, the analyte sensor according to the present invention may be fully or a partially implantable and may, thus, be adapted for performing the detection of the analyte in the body fluid in a subcutaneous tissue, in particular, in an interstitial fluid. Other parts or components may remain outside of the body tissue. For example, as used herein, the terms “implantable” or “subcutaneous” refer to be fully or at least partly arranged within the body tissue of the user. For this purpose, the analyte sensor may comprise an insertable portion, wherein the term “insertable portion” may generally refer to a part or component of an element configured to be insertable into an arbitrary body tissue. The insertable portion comprises the working electrode and typically at least one further electrode, e.g. a counter, reference and/or counter/reference electrode. In certain embodiments, the working electrode is positioned on a first side of the substrate, the at least further electrode is positioned on the second side of the substrate and all electrodes are positioned on the insertable portion. The part of the sensor, which is not inserted, is the upper part of the sensor, which comprises the contacts to connect the sensor to the electronics unit.

Preferably, the insertable portion may fully or partially comprise a biocompatible surface, which may have as little detrimental effects on the user or the body tissue as possible, at least during typical durations of use. For this purpose, the insertable portion may be fully or partially covered with at least one biocompatibility membrane layer, such as at least one polymer membrane, for example a gel membrane which, on one hand, may be permeable for the body fluid or at least for the analyte as comprised therein, and may on the other hand be impermeable for compounds comprised in the analyte sensor, in particular in the working electrode, thus preventing a migration thereof into the body tissue. Further details regarding the biocompatibility membrane layer are disclosed elsewhere herein.

Further, the term “analyte” as used herein is a broad term and is to be given its ordinary and customary meaning to a person of ordinary skill in the art and is not to be limited to a special or customized meaning. The term specifically may refer, without limitation, to an arbitrary element, component or compound which may be present in a body fluid and the concentration of which may be of interest for a user. Specifically, the analyte may be or may comprise an arbitrary chemical substance or chemical compound, which may take part in the metabolism of the user, such as at least one metabolite. As an example, the at least one metabolite may be selected from the group consisting of glucose, cholesterol, triglycerides, lactate; more specifically the analyte may be glucose. Additionally or alternatively, however, other types of analytes and/or any combination of analytes may be determined.

Even further, the term “substrate” as used herein, is a broad term and is to be given its ordinary and customary meaning to a person of ordinary skill in the art and is not to be limited to a special or customized meaning. The term “substrate” is synonymously used with the term “sensor substrate” and specifically may refer, without limitation, to any kind of material or combination of materials, which is suitable to form a carrier layer to support the conductive material and/or the layer of sensing material as described herein. In particular, a “sensor substrate” as understood herein may comprise electrically insulating material.

The term “layer”, as used herein, is a broad term and is to be given its ordinary and customary meaning to a person of ordinary skill in the art and is not to be limited to a special or customized meaning. The term specifically may refer, without limitation, to an element of a layer setup of the analyte sensor. Specifically, the term “layer” may refer to an arbitrary covering of an arbitrary substrate, specifically of a flat substrate. The layer may specifically have a lateral extension exceeding its thickness by at least a factor of 2, at least a factor of 5, at least a factor of 10, or even at least a factor of 20 or more. Specifically, the analyte sensor may have a layer setup. The analyte sensor may comprise a plurality of layers such as the at least one conductive material, the at least one layer of the at least one sensing material, and optionally at least one membrane layer. One or more of the layers of the analyte sensor may comprise sub-layers. For example, a layer comprising the conductive material may comprise at least one further layer.

The term “electrically insulating material”, as used herein, is a broad term and is to be given its ordinary and customary meaning to a person of ordinary skill in the art and is not to be limited to a special or customized meaning. "Electrically insulating material" may also refer to a dielectric material. The term specifically may refer, without limitation, to a material or combination of materials which prevent the transfer of electrical charges and which do not sustain a significant electrical current. Specifically, without limiting other possibilities, the at least one electrically insulating material may be or may comprise at least one insulating resin, such as insulating epoxy resins used in manufacturing electronic printed circuit boards; in particular it may comprise or be a thermoplastic material such as polycarbonate, polyester like polyethylene terephthalate (PET), polyvinyl chloride (PVC), polyurethane, polyether, polyamide, polyimide or a copolymer thereof, such as glycol modified polyethylene terephthalate, polyethylene naphthalate, polytetrafluoroethylene (PTFE) or alumina.

In the method and in the analyte sensor according to the present invention, the sensor substrate may comprise two opposing sides, at least a first side and at least a second side opposing the first side.

Specifically, the analyte sensor, more specifically the sensor substrate, may additionally comprise at least one further electrode, wherein the at least one further electrode may comprise at least one of a reference electrode and a counter electrode. In an embodiment, the at least one further electrode comprises a combined counter/reference electrode. In particular, the reference electrode may comprise at least one reference electrode conductive material; and/or the counter electrode may comprise at least one counter electrode conductive material. More specifically, the at least one further electrode may be disposed on at least one of: the first side and the second side opposing the first side of the sensor substrate.

The term "conductive material", as used herein, is a broad term and is to be given its ordinary and customary meaning to a person of ordinary skill in the art and is not to be limited to a special or customized meaning. The term specifically may refer, without limitation, to a conductive strip, layer, wire or other type of elongated electrical conductor. More specifically, the term "conductive material" may refer, without limitation, to a material, which is conductive and hence capable of sustaining an electrical current, for example the conductive material may comprise at least one material selected from the group consisting of: carbon; carbon paste; gold; copper; silver; nickel; platinum; palladium. Specifically, the conductive material may be or may comprise at least one metal, such as one or more of gold, copper, silver, nickel, palladium or platinum. Additionally or alternatively, the at least one conductive material may be or may comprise at least one conductive compound, such as at least one conductive organic or inorganic compound. Additionally or alternatively, the at least one conductive material may be or may comprise at least one nonmetallic conductive material, e.g. polyaniline, poly-3,4-ethylenedioxythiophene (PEDOT), carbon or carbon paste. Carbon paste specifically may relate to a material comprising carbon, a solvent such as diethylene glycol butyl ether, and at least a binder such as vinyl chloride co- and terpolymers. Preferably, the conductive material according to the present invention may comprise gold and/or carbon; more preferably, the conductive material may consist of gold and/or carbon and/or carbon paste. Specifically the conductive material may comprise gold and a further material, for example carbon.

Moreover, the conductive material may comprise at least one further layer of at least one further material; specifically the further layer may comprise a further conductive material. More specifically the further layer of the conductive material may comprise or may consist of carbon. The further material may be disposed on the first side. Using a further layer, in particular carbon, may contribute to efficient electron transfer by the conductive material.

The conductive material may have a thickness of at least about 0.1 μm, preferably of at least about 0.5 μm, more preferably of at least about 5 μm, specifically of at least about 7 μm, or at least about 10 μm. In the case where the conductive material comprises carbon or is carbon, the conductive material may specifically have a thickness of at least about 7 μm, more specifically of at least about 10 μm, for example about 10 μm to 15 μm. Specifically, in the case where the conductive material is gold, the conductive material may have a thickness of at least about 100 nm, more specifically of at least about 500 nm.

A minimum thickness as specified above may be advantageous as it ensures proper electron transport. A thickness below the specified values is usually not sufficient for reliable electron transport. Even more specifically, the thickness should not exceed a value of about 30 μm in the case of carbon and a value of about 5 μm in the case of gold. If the thickness is too large, the overall thickness and hence the size of the analyte sensor may increase. Larger analyte sensor sizes are generally unwanted as they may cause difficulties when being implanted. Further, they may be less flexible, in particular in the case of carbon and/or they may be expensive, in particular in the case of gold.

The conductive material may be hydrophobic. For example, the contact angle of the conductive material with water may in the range from 60° to 140°, in particular about 100°, determined via microscopy, for example using a Keyence VHX-100, with a water droplet volume of 5 μl.

The conductive material may further comprise a rough surface. A rough surface usually increases the efficiency of electron transfer. Further, it increases the hydrophobicity. A rough surface means that the surface may comprise unevenness. The depth of this unevenness may for example be in the range from 1 μm to 6 μm, such as about 3 μm, determined via light scanning microscopy, in particular via laser scanning microscopy. The distance between two rises in the rough surface may for example be in the range from 20 μm to 80 μm, such as about 40 μm, determined via light scanning microscopy, in particular via laser scanning microscopy.

The terms "reference electrode conductive material" and "counter electrode conductive material", as used herein, are broad terms and are to be given its ordinary and customary meaning to a person of ordinary skill in the art and are not to be limited to a special or customized meaning. The terms specifically may refer, without limitation, to a conductive strip, layer, wire or other type of elongated electrical conductor present on a reference electrode or a counter electrode, respectively. More specifically, the terms may refer, without limitation, to a material, which is conductive, and hence capable of sustaining an electrical current, for example the reference electrode conductive material and/or the counter electrode conductive material may comprise at least one material as specified herein above with respect to the conductive material. In addition to the materials listed above, the reference electrode conductive material and/or the counter electrode conductive material may specifically comprise Ag/AgCl.

The term "sensing material", as used herein, is a broad term and is to be given its ordinary and customary meaning to a person of ordinary skill in the art and is not to be limited to a special or customized meaning.

The sensing material may comprise at least one enzyme; specifically the enzyme is capable of catalyzing a chemical reaction consuming at least the analyte; specifically the enzyme may be an $H_2O_2$ generating and/or consuming enzyme; even more specifically a glucose oxidase (EC 1.1.3.4), a hexose oxidase (EC 1.1.3.5), an (S)-2-hydroxy acid oxidase (EC 1.1.3.15), a cholesterol oxidase (EC 1.1.3.6), a glucose dehydrogenase (EC 1.1.1.47), a galactose oxidase (EC 1.1.3.9), an alcohol oxidase (EC 1.1.3.13), an L-glutamate oxidase (EC 1.4.3.11) or an L-aspartate oxidase (EC 1.4.3.16); even more specifically a glucose oxidase (GOx) including any modification thereof.

In preferred embodiments, the sensing material comprises at least one crosslinker; the crosslinker may for example be capable of crosslinking at least part of the sensing material. Specifically the sensing material may comprise at least one crosslinker selected from UV-curable crosslinkers and chemical crosslinkers; more specifically the sensing material comprises a chemical crosslinker.

In further embodiments, the sensing material does not comprise a crosslinker.

The term "chemical crosslinker" as used herein, is a broad term and is to be given its ordinary and customary meaning to a person of ordinary skill in the art and is not to be limited to a special or customized meaning. The term specifically may refer, without limitation, to a crosslinker that is capable of initiating a chemical reaction generating a crosslinked molecular network and/or a crosslinked polymer when exposed to heat. "Exposed to heat" may refer to being exposed to a temperature above 15° C., specifically to a temperature above 20° C.; more specifically to a temperature in the range from 20° C. to 50° C. and even more specifically to a temperature in the range from 20° C. to 25° C. More specifically, chemical crosslinkers may initiate crosslinking of the layer of the sensing material when exposed to heat.

Suitable chemical crosslinkers according to the present invention are selected from: epoxide based crosslinkers, such as diglycidyl ethers like poly(ethylene glycol) diglycidyl ether (PEG-DGE) and poly(propylene glycol) diglycidyl ether; trifunctional short chain epoxides; anhydrides; diglycidyl ethers such as resorcinol diglycidyl ether, bisphenol, e.g. bisphenol A diglycidyl ether, diglycidyl 1,2-cyclohexanedicarboxylate, poly(ethylene glycol) diglycidyl ether, glycerol diglycidyl ether, 1,4-butanediol diglycidyl ether, poly(propylene glycol) diglycidyl ether, poly(dimethylsiloxane), diglycidyl ether, neopentyl glycol diglycidyl ether, 1,2,7,8-diepoxyoctane, 1,3-glycidoxypropyl-1,1,3,3-tetramethyldisioxane; triglycidyl ethers such as N,N-diglycidyl-4-glycidyloxyaniline, trimethylolpropane triglycidyl ether; tetraglycidyl ethers such as tetrakisepoxy cyclosiloxane, pentaerythritol tetraglycidyl ether, tetraglycidyl-4,4'-methylenebisbenzenamine.

In certain embodiments, the chemical crosslinker is a poly(ethylene glycol) diglycidyl ether (PEG-DGE), particularly PEG-DGE having a number average molecular weight of at least about 200 Da or more, e.g. number average molecular weight of about 500 Da or more.

The term "UV-curable" as used herein, is a broad term and is to be given its ordinary and customary meaning to a person of ordinary skill in the art and is not to be limited to a special or customized meaning. The term specifically may refer, without limitation, to the ability of a chemical substance, for example, a crosslinker, of initiating a photochemical reaction generating a crosslinked molecular network and/or a crosslinked polymer when irradiated by light in the UV spectral range. More specifically, UV-curable crosslinkers may initiate crosslinking of the layer of the sensing material when irradiated by UV light. Crosslinking may in particular be initiated as indicated herein below.

Suitable UV curable crosslinkers according to the present invention include benzophenone, diazirine and azide. Particularly suitable UV-curable crosslinkers are for example selected from the group consisting of, benzophenone comprising crosslinkers, poly(di(2-hydroxy-3-aminobenzo-phenonepropylene)glycol), dibenzophenone 1,2-cyclohexanedicarboxylate, bis[2-(4-azidosalicylamido)ethyl] disulfide, reaction products of the reaction of 4-aminobenzophenone with any one of the above for the chemical crosslinker described diglycidyl crosslinkers, triglycidyl crosslinkers and tetraglycidyl crosslinkers, an example of such a reaction product is 2,4,6,8-tetramethyl-2,4,6,8-tetrakis(2-hydroxy-3-aminpropylbenzophenone)-cyclotetrasiloxane, and reaction products of the reaction of 4-benzoylbenzoic acid N-succinimidyl ester with a diamine or a jeffamine.

Further, the sensing material may comprise at least one polymeric transition metal complex. The term "polymeric transition metal complex" specifically may refer, without limitation, to a material that may be or may comprise at least a polymeric material; specifically it may be or may comprise at least a polymeric material and at least a metal containing complex. The metal containing complex may be selected from the group of transition metal element complexes, specifically the metal containing complex may be selected from osmium-complexes, ruthenium-complexes, vanadium-complexes, cobalt-complexes, and iron-complexes, such as ferrocenes, such as 2-aminoethylferrocene. Even more specifically, the sensing material may comprise a polymeric transition metal complex as described for example in WO 01/36660 A2, the content of which is included by reference. In particular, the sensing material may comprise a modified poly (vinylpyridine) backbone loaded with poly(biimidizyl) Os complexes covalently coupled through a bidentate linkage. A suitable sensing material is further described in Feldmann et al, Diabetes Technology & Therapeutics, 5 (5), 2003, 769-779, the content of which is included by reference. Suitable sensing materials further may include ferrocene-containing polyacrylamide-based viologen-modified redox polymer, pyrrole-2,2'-azino-bis(3-ethylbenzthiazoline-6-sulfonic acid) (ABTS)-pyrene, naphthoquinone-LPEI. The polymeric transition metal complex may represent a redox mediator incorporated into a cross-linked redox polymer network. This is advantageous as it may facilitate electron transfer between the at least one enzyme or analyte and the conductive material. In order to avoid a sensor drift, the redox mediator and the enzyme may be covalently incorporated into a polymeric structure.

In certain embodiments, the at least one enzyme comprised in the sensing material comprises an enzyme capable of catalyzing a chemical reaction consuming at least the analyte, particularly an $H_2O_2$ generating and/or consuming enzyme, a crosslinker and a polymeric transition metal complex. Specifically, the sensing material may comprise at least a polymeric transition metal complex and GOx and a chemical crosslinker. More specifically, the sensing material may comprise a modified poly(vinylpyridine) backbone loaded with poly(bi-imidizyl) Os complexes covalently coupled through a bidentate linkage, GOx and a chemical crosslinker like poly(ethylene glycol) diglycidylether (PEG-DGE). Suitable further sensing materials are known to the person skilled in the art.

In an embodiment, the sensing material may comprise a polymeric material and $MnO_2$-particles.

The sensing material according to the present invention may for example comprise about 40-60 wt % of a polymeric transition metal complex; about 30-40 wt % of an enzyme capable of catalyzing a chemical reaction consuming at least the analyte, particularly a $H_2O_2$ generating and/or consuming enzyme, and about 0.5-25 wt % of a crosslinker based on the dry total weight of the sensing material. When the sensing material is applied in step (b) it may comprise at least one solvent, in particular water. Furthermore, it may comprise the polymeric transition metal complex, the enzyme and the crosslinker. The total concentration of the polymeric transition metal complex, the enzyme and the crosslinker in the at least one solvent, in particular in water, is for example in the range from 10 mg/ml to 200 mg/ml, in particular about 200 mg/ml.

The sensing material which is applied in step (b) may have a viscosity in the range from 10 to 1000 mPas, preferably in the range from 80 to 120 mPas, for example about 100 mPas as determined by a HAAKE™ MARS™ Rheometer (ThermoFisher Scientific).

The method according to the invention may, additionally comprise at least one curing step wherein in the curing step at least a part of the sensing material is crosslinked. The terms “crosslinking” and “curing” are interchangeably used herein. Specifically, the curing step may take place after application and before drying. Further, the curing step may take place before the optional laser irradiation or alternatively, at least partially after performing laser irradiation.

Suitable ways for initiating crosslinking depend on the type of crosslinker and are known by the person skilled in the art. As the preferred crosslinker is a chemical crosslinker, the curing is preferably carried out essentially at room temperature or up to about 90° C., without UV light. Curing using UV-curable crosslinkers is generally induced by irradiation using UV light. As used herein, the term “UV light” generally refers to electromagnetic radiation in the ultraviolet spectral range. The term “ultraviolet spectral range” generally refers to electromagnetic radiation in the range of 1 nm to 380 nm, preferably light in the range of 100 nm to 380 nm.

As further used herein, the term “coating process” may refer to an arbitrary process for applying at least one layer to at least one surface of an arbitrary object. The applied layer may cover the object, for example the conductive material and/or the sensor substrate completely or may only cover a part or parts of the object. The layer may be applied via a coating process wherein a material is provided, e.g. in a liquid form, exemplarily as a suspension or as a solution, and may be distributed on the surface. Specifically, the coating process may comprise a wet-coating process selected from the group consisting of: spin-coating; spray-coating; doctor-blading; printing; dispensing; slot-coating; dip-coating; and cannula-coating.

In particular embodiments, step (b) for applying the sensing material is carried out via cannula-coating. In certain embodiments, the cannula used in the coating process may be a metal cannula or a polymer cannula, e.g. PTFE cannula or a steel cannula. In certain embodiments, the cannula has an wherein the cannula has an inner diameter of about 0.30 mm to about 2 mm, preferably of about 0.3 mm to about 1.3 mm, particularly about 0.33 mm. In certain embodiments, the cannula has a wall strength of about 120 μm to about 180 μm, particularly about 150 μm.

In certain embodiments, the cannula has an outer diameter in the range from 0.55 mm to about 0.70 mm, e.g. about 0.60 mm to about 0.66 mm, particularly about 0.63 mm. It is clear to the skilled person that the inner diameter of the cannula is smaller than the outer diameter of the cannula.

In certain embodiments, the speed of the substrate relative to the cannula during step (b) is in the range from about 1 mm/s to about 30 mm/s, particularly in the range from about 2 mm/s to about 15 mm/s, e.g. about 8 mm/s.

In certain embodiments, the flow rate of the sensing material during step (b) is in the range from about 0.007 ml/min to about 0.30 ml/min, preferably in the range from about 0.01 ml/min to about 0.03 ml/min, particularly of about 0.015 ml/min.

In certain embodiments, the distance between the cannula and the surface of the first side of the substrate to which the sensing material is applied during step (b) is in the range from 20 μm to about 200 μm, preferably in the range from about 50 μm to about 150 μm, particularly about 70 μm.

In certain embodiments, the ratio of the flow rate of the sensing material from the cannula during step (b) to the speed of the substrate relative to the cannula during step (b) is in the range from about 0.01 $mm^2$ to about 0.18 $mm^2$, particularly in the range from about 0.02 $mm^2$ to about 0.09 $mm^2$ (square millimeters).

In certain embodiments, the ratio of the flow rate of the sensing material from the cannula during step (b) to the inner diameter of the cannula is in the range from about 0.09 $mm^2/s$ to about 2.5 $mm^2/s$, particularly from about 0.38 $mm^2/s$ to about 2.27 $mm^2/s$ (square millimeters per second).

In certain embodiments, the ratio of the flow rate of the sensing material from the cannula during step (b) to the speed of the substrate relative to the cannula during step (b) to the inner diameter of the cannula is in the range from about 0.01 mm to about 12.5 mm, particularly from about 0.05 mm to about 0.28 mm.

In step (c) of the method of the invention a working electrode of the analyte sensor is obtained on the first side of the substrate, The term “to obtain at least one working electrode”, as used herein, is a broad term and is to be given its ordinary and customary meaning to a person of ordinary skill in the art and is not to be limited to a special or customized meaning. The term specifically may refer, without limitation, to forming and/or manufacturing the working electrode.

The method according to the present invention may further comprise an additional step of drying the applied layer of the sensing material. The drying step may take place at ambient temperature. Specifically, the sensing material may be dried at ambient temperature for about 10 minutes or less, or about 5 minutes or less, e.g. about 0.5 to about 10 minutes. The term “ambient temperature” as used herein is understood as a temperature specifically between 15° C. and 30° C., more specifically between 20° C. and 25° C.

The method according to the present invention may further comprise an additional step of applying at least one membrane layer, the membrane layer at least partially covering the working electrode. The membrane layer generally may selectively allow for one or more molecules and/or compounds to pass, whereas other molecules and/or compounds are stopped by the membrane layer. Thus, the membrane layer is permeable for the at least one analyte to be detected. Thus, as an example, the membrane layer may be permeable for one or more of glucose, lactate, cholesterol or other types of analytes. The at least one membrane layer may hence function as a diffusion barrier that controls diffusion of the analyte from the exterior, e.g. the body fluid surrounding the analyte sensor, to the sensing material, i. e. the enzyme molecules in the sensing material. In addition, the at least one membrane layer may function as a biocompatibility membrane layer as mentioned elsewhere herein.

The membrane layer, as an example, may have a thickness sufficient for providing mechanical stability. The at least one membrane layer specifically may have a thickness of about 1 μm to about 150 μm. For the at least one membrane layer, as outlined herein, several materials may be used, standalone or in combination. Thus, as an example, the membrane layer specifically may comprise one or more of a polymeric material, specifically a polyvinyl pyridine based copolymer, a polyurethane; a hydrogel; a polyacrylate; a methacrylate-acrylate copolymer or block-copolymer; among which polyvinyl pyridine based copolymers are particularly suitable. These types of membranes are generally known in the art. Moreover, the membrane layer may comprise a crosslinker, specifically a chemical crosslinker or a UV-curable crosslinker, e.g. as described above.

In step (c) of the method according to the invention, in addition to the at least one membrane layer, at least a second membrane layer may be applied. Said second membrane layer may be a biocompatibility membrane layer.

The biocompatibility layer may have a thickness of from about 1 μm to about 10 μm, in an embodiment of from about 3 μm to about 6 μm. More specifically, the biocompatibility layer covers the analyte sensor at least partly or completely. Even more specifically, the biocompatibility layer may be the outmost layer of the analyte sensor. The biocompatibility membrane layer may be or may comprise the following materials: methacrylate based polymers and copolymers, acrylamide-methacrylate based copolymers, biodegradable polysaccharides such as hyaluronic acid (HA), agarose, dextran, chitosan and a poly(vinylpyridine) based polymer.

The at least one membrane layer and/or the biocompatibility membrane layer may be applied by techniques known to those skilled in the art, using at least one coating process, specifically a wet-coating process, selected from the group consisting of: e. g. spin-coating; spray-coating; doctor-blading; printing; dispensing; slot-coating; dip-coating. A preferred wet-coating process is dip-coating or spray-coating.

The method according to the invention may further comprise at least one diffusion step wherein, in the diffusion step the crosslinker comprised in the membrane layer may at least partially diffuse into the sensing material. Diffusion may occur during applying the membrane layer to the sensing material. The diffusion of the crosslinker into the sensing material may allow for at least partial crosslinking of the sensing material independent of the amount of crosslinker in the sensing material during step (b) of applying the sensing material to the substrate.

In the method according to the invention, the diffusion step may further comprise a swelling of at least a part of the sensing material. The term "swelling" as used herein is a broad term and is to be given its ordinary and customary meaning to a person of ordinary skill in the art and is not to be limited to a special or customized meaning. The term specifically may refer, without limitation, to the binding of water and/or to the binding of water-soluble solvent such as ethanol, methanol, acetone to a material, specifically to the binding of water and/or of water-soluble solvent to the sensing material. Due to the uptake of water and/or the uptake of water-soluble solvent into the sensing material, diffusion of the crosslinker into the sensing material may advantageously be enabled which may be required for efficient crosslinking. Swelling may moreover refer to the uptake of water from the membrane layer.

To allow for sufficient swelling in the method according to the present invention, the polymeric material in the sensing material may be capable of taking up of at least 10 wt.-% of water and/or solvent from the membrane layer based on the dry weight of the polymeric material within a time frame of several minutes, e.g. 1 to 15 minutes, more specifically at least 20 wt.-%, even more specifically at least 30 wt.-%, even more specifically up to 90 wt.-%.

This swelling and/or uptake of water and/or solvent is advantageous as diffusing of the crosslinker from the membrane layer into the sensing material may thereby be enabled.

Further, the present invention relates to an analyte sensor comprising at least one working electrode as described above.

The analyte sensor as described herein may in particular be obtainable by the method according to the invention for the preparation of a working electrode on a sensor substrate and a step of providing at least one further electrode, e.g. a counter electrode or a reference electrode or a combined counter/reference electrode.

Moreover, the present invention relates to the use of the analyte sensor for detecting at least one analyte in a sample; specifically in a sample of a body fluid. More particularly, the analyte sensor is a sensor for continuous glucose measurement.

As used herein, the term "body fluid" relates to all bodily fluids of a subject known to comprise or suspected to comprise the analyte of the present invention, including interstitial fluid, blood, plasma, lacrimal fluid, urine, lymph, cerebrospinal fluid, bile, stool, sweat, and saliva. Generally, an arbitrary type of body fluid may be used. Preferably, the body fluid is a bodily fluid which is present in a body tissue of a user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The term "sample" is understood by the skilled person and relates to any sub-portion of a bodily fluid. Samples can be obtained by well-known techniques including, e.g., venous or arterial puncture, epidermal puncture, and the like.

Moreover, the present invention relates to a method for measuring an analyte in a sample comprising the analyte sensor described herein above.

The methods for measuring of an analyte of the present invention, in particular, may be in vivo methods. Alternatively, the method of the invention may also encompass measuring of an analyte under in vitro conditions, e.g. in a sample of a body fluid obtained from a subject, particularly from a human subject. Specifically, said method may not comprise diagnosis of disease based on said measurement.

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments.

Summarizing and without excluding further possible embodiments, the following embodiments may be envisaged:

1. A method for manufacturing a working electrode of an analyte sensor is provided, wherein the method comprises the following steps:

(a) providing a substrate comprising a first side and a second side,
at least one conductive material positioned on the first side of the substrate,
(b) applying a sensing material to an application area on the first side of the substrate, and
(c) obtaining the working electrode of the analyte sensor on the first side of the substrate, wherein the sensing material comprises
at least one enzyme and
at least one cross-linker,
wherein the sensing material is applied in step (b) in a wet layer thickness of greater than about 20 μm in a single application.

2. The method of item 1,
wherein step (b) is performed only once.

3. The method of item 1 or 2,
wherein the at least one conductive material positioned on the first side of the substrate is selected from gold, carbon, carbon paste and any combination thereof.

4. The method of any one of items 1-3,
wherein the sensing material comprises the enzyme glucose oxidase (GOx).

5. The method of any one of items 1-4,
wherein the sensing material comprises at least chemical crosslinker.

6. The method of item 5
wherein the at least one crosslinker is selected from epoxide-based crosslinkers.

7. The method of item 6,
wherein the at least one epoxide-based crosslinker is PEGDGE 500.

8. The method of any one of items 1-7,
wherein the at least one crosslinker is present in the sensing material in an amount of up to about 25% (w/w), particularly from about 0.5% (w/w) to about 25% (w/w) based on the dry weight of the sensing material.

9. The method of any one of items 1-8,
wherein the sensing material further comprises at least one polymeric metal-containing complex.

10. The method of item 9,
wherein the at least one polymeric metal-containing complex is selected from the group of polymeric transition metal-containing complexes.

11. The method of item 10,
wherein the at least one polymeric transition metal-containing complex is selected from osmium-complexes, ruthenium-complexes, vanadium-complexes, cobalt-complex and iron-complexes.

12. The method of any one of items 1-11,
wherein step (b) is carried out via cannula-coating.

13. The method of item 12,
wherein the cannula has an inner diameter of about 0.30 mm to about 2 mm, particularly about 0.33 mm, and/or
wherein the cannula has wall strength of about 120 μm to about 180 μm, particularly about 150 μm, and/or
wherein the cannula has an outer diameter in the range from 0.55 mm to about 0.70 mm, e.g. about 0.60 mm to about 0.66 mm, particularly about 0.63 mm.

14. The method of item 12 or 13,
wherein the speed of the substrate relative to the cannula during step (b) is in the range from about 1 mm/s to about 30 mm/s, particularly in the range from about 2 mm/s to about 15 mm/s, e.g. about 8 mm/s.

15. The method of any one of items 12-14,
wherein the flow rate of the sensing material during step (b) is in the range from about 0.007 ml/min to about 0.3 ml/min, preferably in the range from about 0.01 ml/min to about 0.03 ml/min, particularly of about 0.015 ml/min.

16. The method of any one of items 12-15,
wherein the distance between the cannula and the surface of the first side of the substrate to which the sensing material is applied during step (b) is in the range from 50 μm to about 100 μm, particularly about 70 μm.

17. The method of any one of items 1-16,
wherein after step (b) the sensing material is dried.

18. The method of item 17,
wherein the drying time is about 10 min or less, particularly about 5 min or less.

19. The method of any one of items 1-18,
wherein the layer of the sensing material is applied in a width of about 200 μm to about 600 μm, particularly from about 300 μm to about 500 μm, more particularly about 400 μm.

20. The method of any one of items 1-19,
wherein after drying the sensing material of the working electrode has a dry total thickness in the range from about 3 μm to about 8 μm, particularly from about 3 μm to about 6 μm and more particularly from about 4 μm to about 5 μm.

21. The method of any one of items 1-20,
wherein the edges of the layer of the dried sensing material are steep, particularly wherein the angle between the surface of the substrate and the edge of the sensing material layer is at least about 60°, more particularly at least about 75°.

22. The method of any one of items 1-21,
wherein the cross-section of the layer of the sensing material is substantially a rectangle optionally having an increased height at edges generated by the application of the sensing material onto the application area.

23. The method of any one of items 1-22,
wherein the shape of the layer of the sensing material is substantially a cuboid optionally having an increased height at edges generated by the application of the sensing material onto the application area.

24. The method of any one of items 1-23,
which is carried out continuously.

25. The method of item 24,
wherein the substrate is a raw substrate material, particularly a sheet or a roll onto which the layer of sensing material is applied.

26. A method for manufacturing a working electrode of an analyte sensor is provided,
wherein the method comprises the following steps:
a) providing a substrate comprising
a first side and a second side,
at least one conductive material positioned on the first side of the substrate,
b) applying a sensing material to an application area on the first side of the substrate, and
c) obtaining the working electrode of the analyte sensor on the first side of the substrate, wherein the sensing material comprises at least one enzyme and no cross-linker,
wherein the sensing material is applied in step (b) in a wet layer thickness of greater than about 20 μm in a single application.

27. A method for manufacturing an analyte sensor comprising manufacturing a working electrode according to any one of items 1-26 and providing at least one further electrode.

28. A working electrode of an analyte sensor obtainable by a method of any one of items 1-26.
29. An analyte sensor obtainable by a method of item 27.
30. An analyte sensor comprising:
(i) a substrate comprising
a first side and a second side, and
at least one conductive material positioned on the first side of the substrate,
(ii) a working electrode comprising a sensing material, which at least partially covers the first side of the substrate,
wherein the sensing material forms a layer on the first side of the substrate, wherein the layer of sensing material comprises edges generated by the application of the sensing material onto an application area on the substrate,
wherein the sensing material comprises at least one enzyme and optionally at least one crosslinker,
wherein the layer of sensing material has a dry average total thickness in the range from about 3 μm to about 8 μm, particularly from about 3 μm to about 6 μm and more particularly from about 4 μm to about 5 μm,
and wherein the dry total thickness of the layer of sensing material along at least one of said edges is substantially the same or is increased compared to the dry average total thickness of the layer of the sensing material.
31. The analyte sensor of item 29 or 30,
wherein the dry total thickness of the sensing material at least along one of the edges of the application area, particularly along all edges of the application area, is at least about 75%, at least about 80%, at least about 85%, at least about 90%, at least about 95% and up to about 150%, or up to about 125% compared to the dry average total thickness of the layer of the sensing material (being defined as 100%).
32. The analyte sensor of item 29 or 30,
wherein the dry total thickness of the sensing material at least along one of the edges of the application area, particularly along all edges of the application area, is at least about 125% or at least about 150% compared to the dry average total thickness of the layer of the sensing material (being defined as 100%).
33. The analyte sensor of any one of items 29-32 comprising at least one further electrode, particularly precisely one further electrode.
34. The analyte sensor of item 33,
wherein the at least one further electrode is selected from a counter electrode, a reference electrode and an combined counter/reference electrode.
35. The analyte sensor of any one of items 29-34,
which is a two-electrode sensor comprising precisely one working electrode and one combined counter/reference electrode.
36. Use of an analyte sensor of any one of items 29-35 for detecting at least one analyte in a sample.
37. A method for determining an analyte in a sample comprising using the analyte sensor of any one of items 29-35.

DESCRIPTION OF THE FIGURES

FIG. 1 shows an embodiment of a working electrode comprising a sensing material layer prepared in a single application step with a wet layer thickness of more than 20 μm. An analyte sensor 124 comprises a sensor substrate 114 having a first side 120. The first side 120 comprises at least one conductive material 111 comprising more preferably two materials, e.g. gold and/or carbon. Specifically, the conductive material may comprise a layer of gold 112 and a layer of a further material 110, for example carbon. A sensing material layer 118 applied in a single step onto the conductive material 111 positioned on the first side 120 of the sensor substrate 114 and subsequently dried is shown. The sensing material layer 118 covers at least a portion of the conductive material 111. At the edges 121*a* and 121*b*, a substantial increase in the dry total thickness 125*a*, i.e. in a section spanning a distance of 10 μm from the outermost boundary of the sensing material layer 118 inward, a substantial increase in the dry total thickness 125*a* compared to the dry average total thickness of the sensing material layer 118 and also to the total dry total thickness 125*b* in the central section, i.e. a 10 μm section spanning a distance around the center of the sensing material layer 118, is observed.

Figure 1:
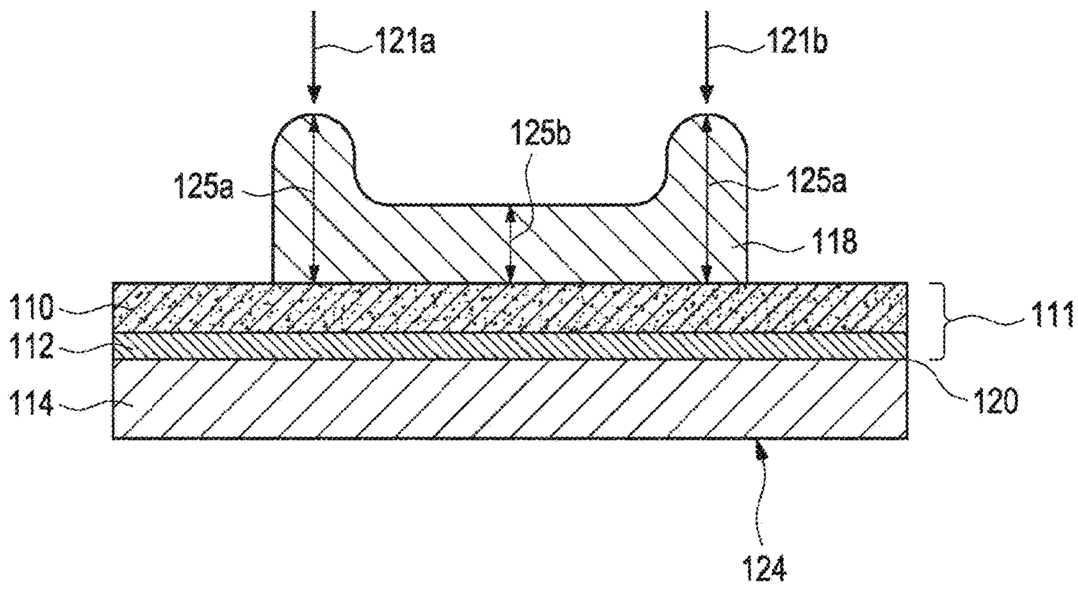
FIG. 1 shows a schematic depiction of a working electrode of the present invention.

In a further embodiment of the invention (not shown), the dry total thickness at the edges may be substantially the same as the dry average total thickness of the sensing material layer.

The analyte sensor 124 is an electrochemical sensor comprising at least one electrode and respective circuitry. More particularly, the analyte sensor 124 is an amperometric electrochemical sensor comprising the at least one working electrode. Typically, the analyte sensor 124 comprises at least one further electrode, particularly a counter electrode and/or a reference electrode and/or a combined counter/reference electrode. The working electrode may be sensitive for the analyte to be measured at a polarization voltage which may be applied between working and reference electrodes and which may be regulated by a potentiostat. A measurement signal may be provided as an electric current between the counter electrode and the working electrode. A separate counter electrode may be absent and a pseudo reference electrode may be present, which may also work as a counter electrode. Thus, an analyte sensor 124 typically may comprise a set of at least two or a set of three electrodes. Specifically, the sensing material 118 is present in the working electrode 122 only.

The invention is not limited to one of the embodiments described above, but is modifiable in a great variety of ways. Those skilled in the art recognize that the embodiments according to the invention can easily be adapted without departing from the scope of the invention. Thus, simple adaptations are conceivable for the preparation of the analyte sensor. The invention enables the preparation of an analyte with reproducible sensor sensitivity at reduced production costs. Further characteristics, details and advantages of the invention follow from the wording of the claims and from the following description of practical examples based on the drawings.

The content of all literature references cited in this patent application is hereby included by reference to the respective specific disclosure content and in its entirety.

EXAMPLES

The following examples serve to illustrate the invention. They must not be interpreted as limiting with regard to the scope of protection.

Example 1: Preparation of a Sensing Material Layer of the Prior Art on a Working Electrode According to the Prior Art A sensor substrate based on polyethylene terephthalate and a thin layer of gold was coated with a carbon paste via doctor blading. Suitable Carbon conductive inks are available from Ercon, Inc. (Wareham, MA), E.I. du Pont de Nemours and Co. (Wilmington, DE), Henkel AG & Co. KGaA, Emca-Remex Products (Montgomeryville, PA), or TEKRA, A Division of EIS, Inc (New Berlin, WI). Afterwards, the carbon paste was dried for 12 h at 50° C.

A layer of sensing material was applied on the sensor substrate by cannula-coating (cannula 1.6 mm (inner diameter), flow rate 0.03 ml/min, speed 8 mm/s, distance between cannula and substrate 30 μm). The sensing material was dried for 3 minutes at 22° C. It was applied in three layers, each with a wet layer thickness of 30 μm.

The sensing material comprised 57% by weight of a polymeric transition metal complex (modified poly (vinylpyridine) backbone loaded with poly(biimidizyl) Os complexes covalently coupled through a bidentate linkage), 33% by weight of glucose oxidase and 10% by weight of PEG-DGE (poly(ethylene glycol)-diglycidylether) in each case based on the sum of the percentages by weight of the polymeric transition metal complex, glucose oxidase and PEG-DGE. Water was used as solvent. The total concentration of the polymeric transition metal complex, glucose oxidase and PEG-DGE in water was 50 mg/ml.

Figure 2:
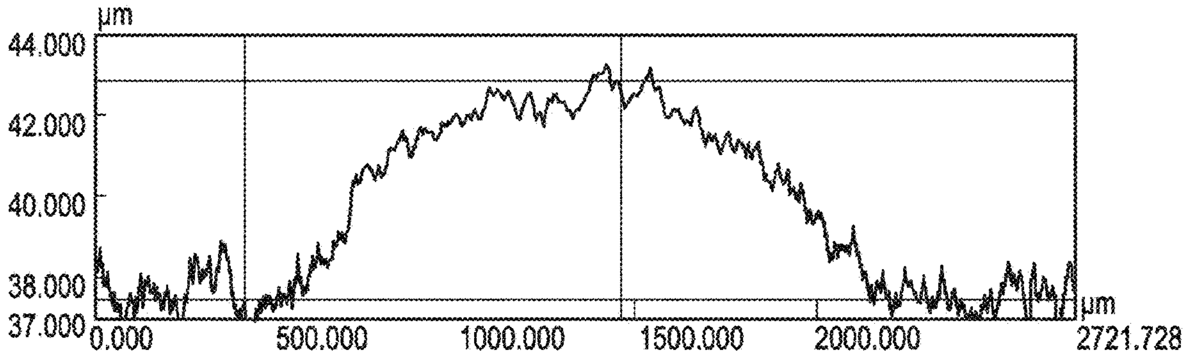
FIG. 2 shows a topographic measurement of the dry total thickness of a working electrode of the prior art.

After drying, a reduced thickness due to spillage at the edges of the sensing material layer was found by a topography measurement on the sensor. The thickness of the sensing material layer was 0-4 μm at the edges being significantly lower than in the in the center region as shown in FIG. 2.

Figure 3:
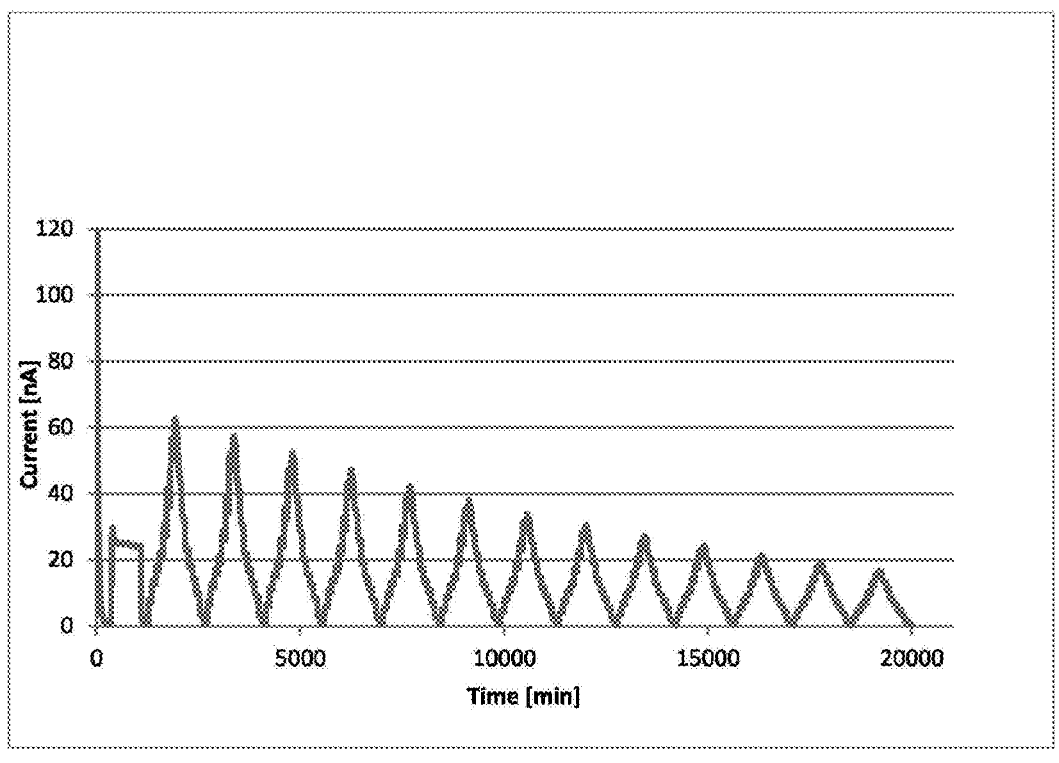
FIG. 3 shows the course of the sensitivity over time for a working electrode of the prior art.

The reduced thickness at the edges has a negative effect on the sensor stability as shown in FIG. 3 by a substantial decrease in the current.

Example 2: Preparation of a Sensing Material Layer on a Working Electrode According to the Present Invention A sensor substrate coated with gold and carbon paste was prepared as described in Example 1.

The sensing material of Example 1 was used.

A layer of sensing material was applied on the sensor substrate by cannula-coating (cannula 0.33 mm (inner diameter), flow rate 0.015 ml/min, speed 8 mm/s, distance between cannula and substrate 70 μm). The sensing material was dried for 3 minutes at 22° C.

Figure 4:
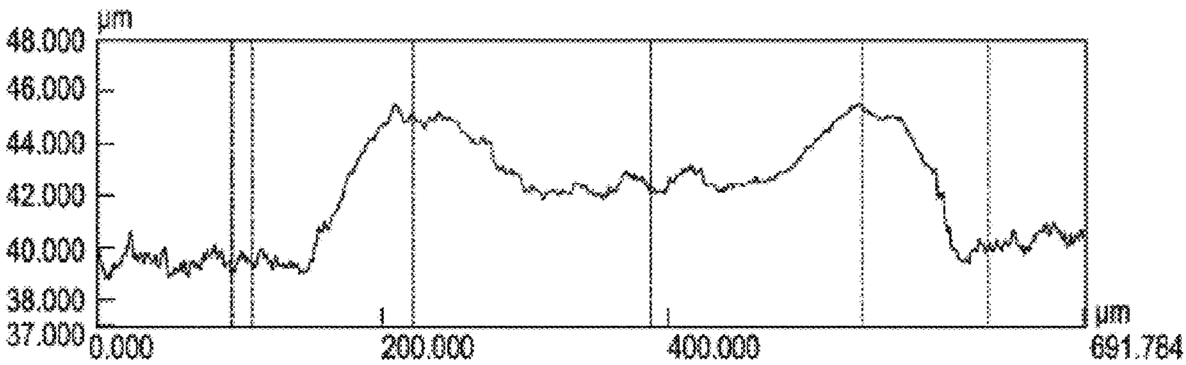
FIG. 4 shows a topographic measurement of the dry total thickness of a working electrode of the present invention.

FIG. 4 shows a topography measurement on a sensor after application of the sensing material. A substantially increased thickness at the edges of the sensing material was found.

Figure 5:
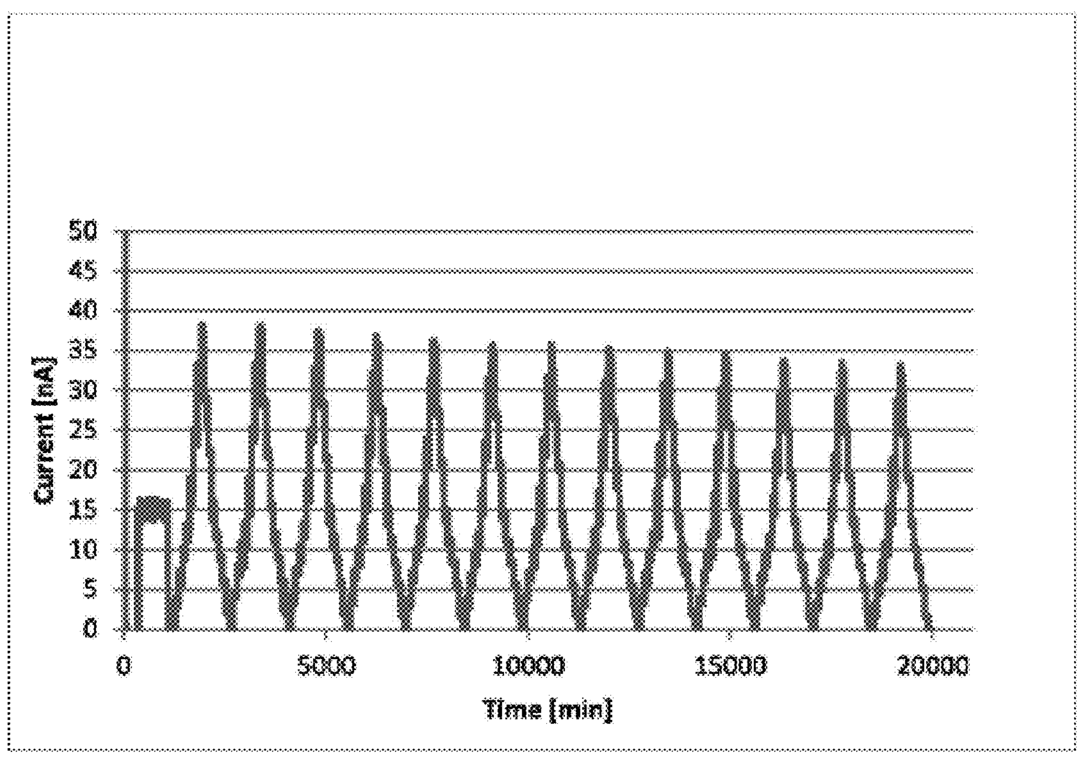
FIG. 5 shows the course of the sensitivity over time for a working electrode of the present invention.

The increased thickness at the edges has a positive effect on the sensor stability as shown in FIG. 5 by a substantially constant current.

Example 3: Variation of Dry Layer Thickness

A sensor substrate coated with gold and carbon paste was prepared as described in Example 1.

The sensing material of Example 1 was used.

The sensing material was applied to the substrate and the dry layer thickness was varied. The sensor drift was determined for the different sensors in a 180 mg/ml solution of glucose, buffered with phosphate over a time range of 14 days. Table 1 shows the average drift per day in % for the different dry layer thicknesses.

TABLE 1

| dry layer thickness | drift % per day |
|---|---|
| 0.5 μm | −20.0 |
| 1.2 μm | −5.0 |
| 2.5 μm | −0.7 |
| 4.0 μm | −0.1 |

The sensor drift is an indicator of the change in sensitivity of the sensor. It can be seen that a dry layer thickness of 2.5 μm or less leads to a significantly increased drift.

The invention claimed is:

1. A method for manufacturing a working electrode of an analyte sensor comprising the following steps:

(a) providing a sheet or roll of a raw substrate material comprising
a first side and a second side,
at least one conductive material being positioned on the first side of the substrate material;
(b) applying via cannula-coating a continuous flow of a sensing material to an application area on the first side of the substrate material; and
(c) obtaining the working electrode of the analyte sensor on the first side of the substrate material,
wherein the sensing material comprises
at least one enzyme and
at least one crosslinker.

2. The method of claim 1, wherein step (b) is performed only once.

3. The method of claim 1, wherein the at least one conductive material positioned on the first side of the substrate material is selected from gold, carbon, carbon paste and any combination thereof.

4. The method of claim 1, wherein the sensing material comprises at least one chemical crosslinker.

5. The method of claim 1, wherein the at least one crosslinker is present in the sensing material in an amount up to about 25% (w/w) based on the dry weight of the sensing material.

6. The method of claim 1, wherein
(i) the cannula has an inner diameter of about 0.3 mm to about 0.4 mm, and/or
(ii) the speed of the substrate material relative to the cannula during step (b) is in the range from about 1 mm/s to about 20 mm/s, and/or
(iii) the flow rate of the sensing material during step (b) is in the range from about 0.007 ml/min to about 0.05 ml/min, and/or
(iv) the distance between the cannula and the surface of the first side of the substrate material to which the sensing material is applied during step (b) is in the range from 50 μm to about 100 μm.

7. The method of claim 6, wherein
the cannula has an inner diameter of about 0.33 mm, and/or
the speed of the substrate material relative to the cannula during step (b) is in the range from about 2 mm/s to about 15 mm/s, and/or the flow rate of the sensing material during step (b) is in the range from about 0.01 ml/min to about 0.03 ml/min.

8. The method of claim 7, wherein the flow rate of the sensing material during step (b) is about 0.015 ml/min.

9. The method of claim 7, wherein the distance between the cannula and the surface of the first side of the substrate material to which the sensing material is applied during step (b) is about 70 μm.

10. The method of claim 1, wherein after step (b) the sensing material is dried.

11. The method of claim 10, wherein after drying the sensing material of the working electrode has a dry total thickness in the range from about 3 μm to about 8 μm.

12. The method of claim 1 and providing at least one further electrode.

13. The method of claim 1, wherein the sensing material comprises PEGDGE 500.

14. The method of claim 1, wherein the at least one crosslinker is present in the sensing material in an amount of about 0.5% (w/w) to about 25% (w/w) based on the dry weight of the sensing material.

15. The method of claim 1, wherein after drying the sensing material of the working electrode has a dry total thickness in the range from about 3 μm to about 6 μm.

16. The method of claim 15, wherein after drying the sensing material of the working electrode has a dry total thickness in the range from about 4 μm to about 5 μm.

17. The method of claim 16, wherein the obtaining of the working electrode comprises cutting the raw substrate material into pieces having the desired size.

18. The method of claim 1 wherein the sensing material is applied as a wet layer.

19. The method of claim 18 wherein the sensing material is applied having a wet layer thickness greater than about 20 μm in a single application.

20. The method of claim 1 wherein the cannula-coating comprises moving the sheet or roll relative to a cannula and continuously flowing the sensing material from the cannula onto the application area.

21. The method of claim 20 wherein the raw substrate material comprises numerous aligned working electrodes and the sensing material is applied continuously onto the aligned working electrodes.

22. The method of claim 20 wherein the cannula-coating is applied as a continuous flow onto the sheet or roll as a wet layer having a wet layer thickness of greater than 20 μm.

* * * * *